United States Patent [19]

Grütter et al.

[11] Patent Number: 5,079,229
[45] Date of Patent: Jan. 7, 1992

[54] MODIFIED EGLIN PROTEINS

[75] Inventors: Markus G. Grütter, Hochwald, Switzerland; Dirk Heinz, Rheinfelden, Fed. Rep. of Germany; Manfred Liersch, Riehen, Switzerland

[73] Assignee: Ciba-Geigy Corporation, Ardsley, N.Y.

[21] Appl. No.: 320,139

[22] Filed: Mar. 7, 1989

[30] Foreign Application Priority Data

Mar. 7, 1988 [CH] Switzerland .......................... 840/88

[51] Int. Cl.$^5$ .......................... C07K 7/10; A61K 37/64
[52] U.S. Cl. .................................. 514/12; 530/324; 530/855; 435/69.2
[58] Field of Search ................. 530/324, 855; 514/12; 435/69.2

[56] References Cited

U.S. PATENT DOCUMENTS

| | | | |
|---|---|---|---|
| 4,636,489 | 1/1987 | Seemüller et al. | 514/12 |
| 4,711,848 | 12/1987 | Insley et al. | 435/91 |

FOREIGN PATENT DOCUMENTS

| | | |
|---|---|---|
| 100561 | 2/1984 | European Pat. Off. |
| 134479 | 3/1985 | European Pat. Off. |
| 146785 | 7/1985 | European Pat. Off. |
| 164719 | 12/1985 | European Pat. Off. |
| 238993 | 9/1987 | European Pat. Off. |
| 278112 | 12/1987 | European Pat. Off. |
| WO86/03519 | 6/1986 | PCT Int'l Appl. |

OTHER PUBLICATIONS

Bode et al., *EMBO J.*, 5:813-818 (1986).
Bode et al., *Eur. J. Biochem.*, 166:673-692 (1987).
Schnebli, "Eglin C: An Elastase/Cathepsin G Inhibitor with Therapeutic Potential in Emphysema and ARDS: A Review", in *Pulmonary Emphysema and Proteolysis:* 1986 (Academic Press, Inc. 1987) pp. 73-84.
Chem. Abstract of EP 146,785.
Heinz et al., Methods in Protein Sequence Analysis, 7th International Conference, Ed. B. Wittmann-Liebold, pp. 415-422 (1988).
Carell, R. W. (1986) Biotechnology and Genetic Engineering Reviews 4, 291-309.
Matheson, N. R. et al, (1986) J. Biological Chemistry 261, 10404-10409.
Courtney, M. et al., (1985) Nature 313, 149-151.
Courtney, M. et al. (1986) Phil. Trans. R. Soc. Lond., A317, 381-390.
Courtney, M. (1986) World Biotech Report 1, B21-B26.
Courtney, M. (1987) World Biotech. Report 1, 163-170.
Travis, J. et al. (1985) J. Biological Chemistry 260, 4384-4389.
Laskowski, M. et al. (1987) Abstr. Pap. Am. Chem. Soc., Conference Abstract, MBTB 190.
Holmes, W. E. et al. (1987) Biochemistry 26, 5133-5140.
Heinz et al., Methods in Protein Sequence Analysis, 7th International Conference, Ed. by Weitmann-LIebold, pp. 415-422 (1988).

*Primary Examiner*—Margaret Moskowitz
*Assistant Examiner*—Nina Ossanna
*Attorney, Agent, or Firm*—Shawn P. Foley; JoAnn Villamizar

[57] ABSTRACT

Novel elgin mutants that differ from the natural eglins B and C by the replacement of one, two or three amino acids in the region of the active center (amino acids 45 and 46, Leu-Asp) by other amino acids are provided. The mutants, which can be produced by recombinant genetic engineering, have valuable pharmacological properties.

3 Claims, No Drawings

MODIFIED EGLIN PROTEINS

The invention relates to mutants of the protease inhibitors eglin B and eglin C, to hybrid vectors suitable for the production of such mutants and to host microorganisms transformed with such hybrid vectors, as well as to processes for the production of the said hybrid vectors, transformed host microorganisms and eglin mutants.

Two protease inhibitors isolated from leeches (Hirudo medicinalis), designated eglin B and eglin C, are described in German Offenlegungsschrift No. 2808396. These polypeptides each consist of 70 amino acids, have a molecular weight of approximately 8100 and are strong inhibitors of chymotrypsin, subtilisin, of the animal and human granulocyte proteases elastase and cathepsin G and also of the mast cell protease chymase. By contrast, proteases similar to trypsin are not inhibited or are inhibited only to an insignificant degree.

Eglin C has the following primary structure:

H—ThrGluPheGlySerGluLeuLysSerPheProGluValValGlyLys—
ThrValAspGlnAlaArgGluTyrPheThrLeuHisTyrProGlnTyrAsp—
ValTyrPheLeuProGluGlySerProValThrLeuAspLeuArgTyrAsn—
ArgValArgValPheTyrAsnProGlyThrAsnValValAsnHisValPro—
HisValGly—OH

Eglin C, unlike most of the known protease inhibitors, does not contain any disulfide bridges. Taking into consideration its relatively small molecular size it is unusually stable in respect of denaturation by acid, alkali hydroxide solution or heat and in respect of proteolytic degradation. The primary structure of eglin B differs from that of eglin C by the replacement of amino acid 35, tyrosine, by histidine.

Eglins are to date amongst the strongest known inhibitors of human and animal granulocyte elastase and of human granulocyte cathepsin G. Uncontrolled or excessive release of these cellular proteases in the organism can intensify an inflammatory process and cause tissue destruction by non-specific proteolysis. These enzymes, which are responsible for intracellular digestion, are optimally active in a physiological (neutral to weakly alkaline) medium and enable native tissue substances (for example elastin) and humoral factors (for example blood coagulation factors and complement factors) rapidly to be destroyed and inactivated. Because of their hitherto known properties eglins are therefore of considerable interest for use in medicinal therapy anti-inflammatory, antiphlogistic, septic shock, pulmonary emphysema, mucoviscidosis etc.).

It has recently become possible to obtain eglins by recombinant genetic engineering processes (cf. European Patent Application No. 146785).

The problem underlying the invention is to produce novel protease inhibitors starting from eglin B or eglin C.

This problem has been solved in accordance with the invention by the provision of eglin mutants that differ from the natural eglins B and C by the replacement of one, two or three amino acids in the region of the active centre (amino acids 45 and 46, Leu-Asp) by other amino. The eglin mutants so obtained in accordance with the invention exhibit surprising properties: compared with eglin B and eglin C they are distinguished by an increased specificity in the inhibition of certain proteases, or by the inhibition of proteases that are not inhibited or are scarcely inhibited by eglins B and C, for example trypsin or thrombin.

The invention relates especially to eglin mutants of the formula

R—ThrGluPheGlySerGluLeuLysSerPheProGluValValGlyLys— (I)
ThrValAspGlnAlaArgGluTyrPheThrLeuHisTyrProGlnTyrAsp—
Val—W—PheLeuProGluGlySerProVal—X—Y—Z—LeuArg—
TyrAsnArgValArgValPheTyrAsnProGlyThrAsnValValAsn-
His—
ValProHisValGly—OH, in which R is hydrogen or acetyl, W is Tyr or His, X is Thr, Ser or Pro, Y is Leu, Met, Arg, Lys, Phe, Tyr or Trp, and Z is Asp, Glu, Gln, Asn, Ala, Ser or Thr, with the proviso that X is other than Thr when Y is Leu and Z is Asp, and salts thereof.

The invention relates especially to compounds of the formula I in which R is acetyl, W is Tyr and either X is Thr, Y is Arg or Lys and Z is Asp, Glu, Gln, Asn, Ala, Ser or Thr, or X is Pro, Y is Met and Z is Asp, or X is Thr, Y is Phe, Tyr, Trp or Met and Z is Asp, and salts thereof.

The invention relates chiefly to compounds of the formula I in which R is acetyl, W is Tyr, X is Thr, Y is Arg and Z is Asp or Ser, and salts thereof.

The invention relates especially to a compound of formula I in which R is acetyl, W is Tyr, X is Thr, Y is Arg and Z is Asp, and salts thereof.

The novel compounds of the formula I can be not only in free form, but also in the form of their salts, especially their pharmaceutically acceptable salts. Since they contain several amino acid residues having free amino groups or guanidino groups, the compounds of the invention may, for example, be in the form of acid addition salts. Suitable acid addition salts are especially physiologically tolerable salts with customary therapeutically acceptable acids. Suitable inorganic acids are hydrohalic acids (such as hydrochloric acid) but also sulfuric and phosphoric or pyrophosphoric acid; suitable organic acids are especially sulfonic acids (such as benzene or p-toluenesulfonic acid or lower alkanesulfonic acids, such as methanesulfonic acid) and also carboxylic acids, such as acetic acid, lactic acid, palmitic and stearic acid, malic acid, tartaric acid, ascorbic acid and citric acid. Since the eglin compounds also contain amino acid residues having free carboxy groups, they may also be in the form of metal salts, especially alkali metal or alkaline earth metal salts, for example sodium, potassium, calcium or magnesium salts, or in the form of ammonium salts, derived from ammonia or from a physiologically tolerable organic nitrogen-containing base. Since they may, however, contain free carboxy groups and free amino (and guanidino) groups simultaneously, they may also be present in the form of internal salts.

The eglin mutants of the invention and salts thereof can be produced according to processes that are known per se, for example by genetic engineering processes, for example by culturing a transformed host microorganism containing a DNA that codes for one of the mentioned eglin mutants and isolating the eglin mutant or a salt thereof. The eglin mutants of the invention and salts thereof are produced especially by a. producing a DNA that codes for the eglin mutant,
b. inserting this DNA into a vector,
c. introducing the resulting hybrid vector into a host microorganism by transformation, d. culturing the transformed host microorganism under conditions that permit expression of the eglin mutant, and e. isolating the eglin mutant or a salt thereof.

DNAs CODING FOR EGLIN MUTANTS

The invention relates to DNAs containing a nucleotide sequence that codes for an elgin mutant, especially for one of the eglin mutants mentioned above as being especially preferred.

The DNAs of the invention preferably have at their ends flanking sequences that include suitable restriction sites and that render possible the insertion of the DNA into a vector.

The DNAs of the invention can be produced according to processes that are known per se. For example, the DNAs can be produced chemically, or fragments thereof can be produced by chemical synthesis and linked enzymatically in a predetermined manner, or a DNA coding for eglin B or eglin C can be mutated in one or more steps.

The chemical synthesis of DNAs is carried out by processes that are known per se. Suitable procedures are described by S.A. Narang [Tetrahedron 39, 3 (1983)] and in European Patent Application No. 146785.

The production of the DNAs of the invention can also be effected by mutation of the DNA coding for eglin B or eglin C. Preferably, the process known as "site directed mutagenesis" is used [cf. M.J. Zoller et al., Meth. Enzym. 100, 468 (1983)]. In this process single-stranded eglin DNA is cloned in bacteriophage M13, hybridised with a complementary oligonucleotide that contains the nucleotide(s) directing the mutation, the hybridisation product is supplemented to form the double strand, the resulting double-stranded bacteriophage is introduced by transformation into a suitable Escherichia coli host and, after culturing the transformed E. coli cells, those cells that contain the DNA coding for the eglin mutant are identified by hybridisation with the above-mentioned oligonucleotide.

PRODUCTION OF EXPRESSION VECTORS THAT CONTAIN A DNA CODING FOR AN EGLIN MUTANT

The invention relates furthermore to expression vectors that contain a DNA sequence coding for an eglin mutant, which DNA sequence is regulated in such a manner by an expression control sequence that the eglin mutant is expressed in a host cell transformed with those expression vectors.

The expression vectors of the present invention are produced, for example, by so inserting a DNA sequence coding for the eglin mutant into a vector DNA that contains an expression control sequence that the expression control sequence regulates the said DNA sequence.

The choice of a suitable vector is based on the host cell provided for the transformation. Suitable hosts are, for example, microorganisms, such as yeasts, for example *Saccharomyces cerevisiae*, and especially strains of bacteria, especially strains of *Escherichia coli*, and also Bacillus subtilis, as well as cells of higher organisms, especially established human or animal cell lines. Preferred host cells are strains of *E. coli*.

In principle any vector is suitable that replicates and expresses in the selected host the DNA sequences of the invention coding for the eglin mutants.

Examples of vectors that are suitable for the expression of the eglin mutants in an *E. coli* strain are bacteriophages, for example derivatives of bacteriophage, or plasmids, such as, especially, plasmid col E1 and its derivatives, for example pMB9, pSF2124, pBR317 or pBR322. The preferred vectors of the present invention are derived from plasmid pBR322. Suitable vectors contain a complete replicon and a marker gene that renders possible the selection and identification of the microorganisms transformed with the expression plasmids by means of a phenotypic marker. Suitable marker genes impart to the microorganism, for example, resistance to heavy metals, antibiotics and the like. Furthermore, preferred vectors of the present invention contain apart from the replicon and marker gene regions recognition sequences for restriction endonucleases, so that the DNA sequence coding for the eglin mutant and, where appropriate, the expression control sequence, can be inserted at those sites.

Several expression control sequences can be used to regulate the expression. The expression control sequences used are especially those of strongly expressed genes of the host cell that is to be transformed. In the case where pBR322 is used as the hybrid vector and *E. coli* is used as the host microorganism, suitable expression control sequences (which contain, inter alia, the promoter and the ribosomal binding site) are, for example, those of lactose operon, tryptophan operon, arabinose operon and the like, of the β-lactamase gene, and the corresponding sequences of the phage N-gene or of the phage fd-layer protein gene, and others. Whereas the promoter of the β-lactamase gene (β-lac-gene) is already contained in plasmid pBR322, the other expression control sequences must be inserted into the plasmid. The expression control sequence preferred in the present invention is that of tryptophan operon (trp po).

Vectors suitable for replication and expression in yeast contain a yeast replication start and a selective genetic marker for yeast. Hybrid vectors that contain a yeast replication start, for example the chromosomal autonomously replicating segment (ars), are retained extrachromosomally within the yeast cell after the transformation and are replicated autonomously during mitosis. Furthermore, hybrid vectors that contain sequences homologous to the yeast 2 μ-plasmid DNA may be used. Such hybrid vectors are incorporated by recombination within the cell with 2 μ plasmids already present or are replicated autonomously. Suitable marker genes for yeast are especially those that impart antibiotic resistance to the host or, in the case of auxotrophic yeast mutants, genes that complement host defects. Corresponding genes impart, for example, resistance to the antibiotic cycloheximide or provide for prototrphy in an auxotrophic yeast mutant, for example the ura 3, leu 2, his 3 or, especially, trp 1 gene. Preferably, yeast hybrid vectors furthermore contain a replication start and a marker gene for a bacterial host, especially *E. coli*, so that the construction and cloning of the hybrid vectors and their precursors can be carried out in a bacterial host. Expression control sequences suitable for expression in yeast are, for example, those of the trp 1, adh I, adh II or pho 5 gene, and also promoters involved in glycolytic degradation, for example the pgk and the gapdh promoter.

The invention relates especially to expression vectors capable of replication and phenotypic selection that contain an expression control sequence and a DNA sequence coding for the eglin mutant, the said DNA sequence together with a transcription start signal and termination signal as well as a translation start signal and stop signal being so arranged in said expression plasmid under the regulation of the said expression control sequence that the eglin mutant is expressed in a host cell transformed with said expression plasmid.

To achieve an effective expression, the gene coding for the eglin mutant must be arranged correctly (in "phase") with the expression control sequence. It is advantageous to link the expression control sequence, in the region between the main mRNA start and the ATG of the gene coding sequence that is naturally linked to the expression control sequence (for example the β-lac coding sequence if using the β-lac promoter), to the eglin mutant gene, which preferably brings with it its own translation start signal (ATG) and translation stop signal (for example TAG). By this means effective transcription and translation is ensured.

TRANSFORMATION OF MICROORGANISMS

The invention relates also to a process for the production of transformed host cells, which comprises transforming a host cell with an expression vector containing a DNA sequence that codes for the eglin mutant and that is regulated by an expression control sequence.

Suitable host cells are, for example, the above-mentioned microorganisms, such as strains of *Saccharomyces cerevisiae*, *Bacillus subtilis* and especially *Escherichia coli*. The transformation with the expression plasmids of the invention is carried out, for example, in the manner described in the literature, for example for *S. cerevisiae* [A. Hinnen et al., Proc. Natl. Acad. Sci. U.S.A 75, 1929, (1978)], *B. subtilis* (Anagnostopoulos et al., J. Bacteriol. 81, 741 (1961)] and *E. coli*. [M. Mandel et al., J. Mol. Biol. 53, 159 (1970)]. The transformed host cells are advantageously isolated from a selective nutrient medium to which is added the biocide against which the marker gene contained in the expression plasmid imparts resistance. Cells that do not contain the expression plasmid are killed in such a medium.

The invention also relates to the transformed host cells obtainable by the said method.

Culturing the transformed host cells and recovering the eglin mutants. The transformed host cells are used to produce the eglin mutants. The process for the production of the eglin mutants comprises culturing the above-mentioned transformed host cells and freeing and isolating the product from the host cells.

The invention relates especially to a process for producing eglin mutants of the formula I and salts of such compounds which comprises culturing in a liquid nutrient medium that contains assimilable carbon and nitrogen sources, host cells transformed with an expression plasmid containing a DNA sequence that codes for an eglin mutant of the formula I and that is regulated by an expression control sequence, and freeing and isolating the product from the host cells and, if desired, separating a mixture of compounds of the formula I obtained according to the process into the individual components and, if desired, converting a resulting salt into the free polypeptide or a resulting polypeptide into a salt.

The transformed host cells of the invention are cultured in a manner known per se. For example, various carbon sources can be used for culturing the transformed host microorganisms of the invention. Examples of preferred carbon sources are assimilable carbohydrates, such as glucose, maltose, mannitol or lactose, or an acetate that can be used either on its own or in suitable mixtures. Suitable nitrogen sources are, for example, amino acids, such as casamino acids, peptides and proteins and their degradation products, such as tryptone, peptone or meat extracts; furthermore, yeast extracts, malt extract, as well as ammonium salts, for example ammonium chloride, sulfate or nitrate, which can be used either on their own or in suitable mixtures. Inorganic salts, which can also be used, are, for example, sulfates, chlorides, phosphates and carbonates of sodium, potassium, magnesium and calcium.

Furthermore, the medium contains, for example, growth-promoting substances, such as trace elements, for example iron, zinc, manganese and the like, and preferably substances that exert a selection pressure and prevent the growth of cells that have lost the expression plasmid. For example ampicillin is added to the medium when the expression plasmid contains an ampR gene. Such an addition of antibiotically active substances also has the effect of killing contaminating microorganisms that are sensitive to antibiotics.

Culturing is carried out according to processes that are known per se. The culturing conditions, such as temperature, pH value of the medium and frementation time, are so selected that maximum titres of eglin mutants are obtained. For example an *E. coli* or a yeast strain is preferably cultured under aerobic conditions in submersed culture with shaking or stirring at a temperature of approximately from 20° to 40° C., preferably approximately 30° C., and a pH value of from 4 to 9, preferably pH 7, for approximately from 4 to 20 hours, preferably from 8 to 12 hours. The expression product accumulates intracellularly.

When the cell density has reached a suitable value, culturing is interrupted and the product is freed from the cells of the microorganism. For this purpose the cells are broken down, for example by treatment with a detergent, such as SDS or Triton, or are lysed with lysozyme or a similarly acting enzyme. Alternatively, or in addition, mechanical forces, such as shearing forces (for example X-press, French press, Dyno-Mill) or agitation with glass beads or aluminium oxide, or alternate freezing, for example in liquid nitrogen, and thawing, for example to 30° to 40° C., as well as ultrasound, are used to break open the cells. After centrifugation, the proteins of the resulting mixture, which contains proteins, nucleic acids and other cell components, are enriched in a manner known per se. For example, the majority of the non-protein components can be separated off by polyethyleneimine treatment and the proteins, including the eglin compounds, precipitated, for example by saturating the solution with ammonium sulfate or with other salts. Bacterial proteins can also be precipitated by means of acidification with acetic acid (for example 0.1%, pH 3–5). A further enrichment of eglin mutants can be achieved by extracting the ethyl acetate supernatant with n-butanol. Other purification steps include, for example, chromatographic processes, such as ion exchange chromatography, gel filtration, gel permeation chromatography, partition chromatography, HPLC, reversed phase HPLC and the like. For example, after charging by means of gel or carrier-free electrophoresis, the mixed components are separated by dialysis according to molecular size using a suitable Sephadex column, or the components are separated by affinity chromatography, for example with antibodies, especially monoclonal antibodies, or with anhydrochymotrypsin or thrombin coupled to a carrier suitable for affinity chromatography, or by further processes, especially those known from the literature.

For example, the isolation of the expressed eglin mutants comprises the following steps:

separation of the cells from the culture solution by means of centrifugation, production of a crude extract by breaking down the cells, for example by means of a Dyno-Mill, removal of the insoluble components by centrifugation; precipitation of the bacterial proteins by means of 1% acetic acid, gel filtration on Sephadex G50 (or G75) and, if appropriate, reversed phase HPLC. The removal of salts is carried out, for example, on Sephadex G25.

The test with anti-eglin antibodies, such as polyclonal antibodies obtainable from rabbits or monoclonal antibodies obtainable from hybridoma cells, for example the monoclonal antibodies secreted by hybridoma cell lines 299S18-20 (CNCM I-361), 299S20-1 (CNCM I-362) or 299S20-10 (CNCM I-363), or the inhibition of target proteases, for example human leukocyte elastase (HLE) or cathepsin G (Cat G) [cf. U. Seemüller et al., Hoppe-Seyler's Z. physiol. Chem. 358, 1105 (1977); U. Seemüller et al., Meth. Enzym. 80, 804 (1981)], can be used to detect the eglin mutants.

A mixture of compounds of the formula I obtainable in accordance with the process, for example consisting of compounds of the formula I in which R is either H or acetyl, can be separated into the individual components in a manner known per se. Suitable separating processes are, for example, chromatographic processes, for example adsorption chromatography, ion exchange chromatography, HPLC or reversed phase HPLC, also multiplicative partitioning or electrophoretic methods, for example electrophoresis on cellulose acetate or gel electrophoresis, especially polyacrylamide gel electrophoresis ("PAGE").

Depending upon the procedure, the compounds of the invention are obtained in free form or in the form of acid addition salts, internal salts or salts with bases. The free compounds can be obtained from the acid addition salts in a manner known per se. In turn it is possible to obtain therapeutically acceptable acid addition salts or metal salts from the free compounds by reaction with acids or bases, for example with those that form the above-mentioned salts, and by concentration by evaporation or lyophilisation. The internal salts can be obtained by adjusting the pH to an appropriate neutral point.

Pharmaceutical Preparations

The novel eglin mutants of the formula I have valuable pharmacological properties and can be used in the prophylaxis or treatment of disease conditions that require the use of protease inhibitors.

The novel eglin mutants exhibit as protease inhibitors an activity profile that differs from that of the natural eglins B and C as follows:

the inhibiting action on certain proteases is increased, or certain of the proteases not inhibited by the natural eglins are strongly inhibited whilst the inhibiting action against some natural target proteases of eglins, such as, for example, granulocyte elastase, is weakened or has disappeared. For example, compounds of the formula I in which R is hydrogen or acetyl, W is Tyr or His, X is Pro, Y is Met and Z is Asp exhibit an increased inhibition of human and animal granulocyte elastase compared with the natural eglins and accordingly, like the natural eglins, can be used, for example, in the treatment of pulmonary emphysema, ARDS ("acute respiratory distress syndrome"), septic shock rheumatic arthritis and mucoviscidosis. Unlike the natural eglins, compounds of the formula I in which R and W have the meanings given for formula I, X is Thr, Y is Arg or Lys and Z is Asp, exhibit a pronounced inhibitory action on trypsin and only a slight action against granulocyte elastase and cathepsin G. This applies especially to the compound of formula I in which R is acetyl, W is Tyr, X is Thr, Y is Arg and Z is Asp. Such compounds can, analogously to aprotinin, be used, for example, for the treatment of pancreatitis and of traumatic pancreatogenous and haemorrhagic shock. Compounds of the formula I in which R, W and X have the meanings given for formula I, Y is Arg or Lys and Z is Asp have a pronounced inhibitory action on thrombin and can be used, preferably in combination with antithrombin III, for example, for the treatment of thromboses, thromboembolisms, septic and post-traumatic shock and coagulopathies.

The invention relates also to pharmaceutical compositions that contain at least one of the compounds of the invention or pharmaceutically acceptable salts thereof, where appropriate together with a conventional pharmaceutically acceptable carrier and/or adjuncts.

These compositions may be used especially in the case of the abovementioned indications when administered, for example, parenterally, such as intravenously, intracutaneously, subcutaneously or intramuscularly, or topically.

The invention relates also to the use of the novel compounds of the invention and of pharmaceutical compositions containing them for the prophylactic and therapeutic treatment of the human or animal body, especially in the case of the above-mentioned syndromes.

The dosage depends especially on the specific form of administration and on the purpose of the treatment or prophylaxis. The size of a single dose and the administration schedule can best be determined on the basis of an individual assessment of the particular disorder presented; the requisite methods for determining relevant factors, such as blood factors, are familiar to the skilled person.

In the case of thrombin-inhibiting eglin mutants, the therapeutically effective amount in the case of an injection is in a dosage range of from approximately 0.005 to approximately 0.1 mg/kg body weight. A range of from approximately 0.01 to approximately 0.05 mg/kg body weight is preferred. Administration is carried out by intravenous, intramuscular or subcutaneous injection. Accordingly, pharmaceutical preparations for parenteral administration in single dose form contain from approximately 0.4 to approximately 7.5 mg of the compound of the invention per dose depending on the mode of administration. In addition to the active ingredient these pharmaceutical compositions usually also contain a buffer, for example a phosphate buffer, to keep the pH value between approximately 3.5 and 7, and also sodium chloride, mannitol or sorbitol to set the isotonicity. They may be in freeze-dried or dissolved form, and solutions may with advantage contain an antibacterially active preservative, for example from 0.2 to 0.3% 4-hydroxybenzoic acid methyl ester or ethyl ester.

A preparation for the topical use of thrombin-inhibiting eglin mutants may be in the form of an aqueous solution, lotion or jelly, an oily solution or suspension, or a fat-containing ointment or, especially, an emulsified ointment. A preparation in the form of an aqueous solution is obtained, for example, by dissolving an active ingredient of the invention, or a therapeutically acceptable salt thereof, in an aqueous buffer solution of pH 4 to 6.5 and, if desired, adding a further active ingredient, for example an anti-inflammatory, and/or a polymeric tackifier, for example polyvinylpyrrolidone, and/or a preservative. The concentration of the active ingredient is from approximately 0.1 to approximately 1.5 mg, preferably from 0.25 to 1.0 mg, per 10 ml of solution or 10 g of jelly. An oily form of application for topical administration is obtained, for example, by suspending an active ingredient of the invention or a therapeutically acceptable salt thereof in an oil, where appropriate with the addition of swelling agents, such as aluminium stearate, and/or surface-active agents (surfactants) of which the HLB value ("hydrophilic-lipophilic balance") is below 10, such as fatty acid monoesters of polyhydric alcohols, for example glycerol monostearate, sorbitan monolaurate, sorbitan monostearate or sorbitan monooleate. A fat-containing ointment is obtained, for example, by suspending an active ingredient of the invention or a salt thereof in a spreadable fatty base, where appropriate with the addition of a surfactant having an HLB value below 10. An emulsified ointment is obtained by triturating an aqueous solution of an active ingredient of the invention or a salt thereof in a soft, spreadable fatty base with the addition of a surfactant of which the HLB value is below 10. All of these topical forms of application may also contain preservatives. The concentration of the active ingredient is from approximately 0.1 to approximately 1.5 mg, preferably from 0.25 to 1.0 mg, per approximately 10 g of the base material.

The administration of elastase-inhibiting eglin mutants is effected by intravenous injection or intrapulmonarily, by inhalation, for example using a Bird device. Accordingly, pharmaceutical preparations for parenteral administration in single dose form contain approximately from 10 to 50 mg of a compound of the invention per dose, depending on the mode of application. In addition to the active ingredient these pharmaceutical compositions usually also contain sodium chloride, mannitol or sorbitol for setting the isotonicity. They may be in freeze-dried or dissolved form, and solutions may with advantage contain an antibacterially active preservative, for example from 0.2 to 0.3% 4-hydroxybenzoic acid methyl ester or ethyl ester.

Preparations for the topical use of elastase-inhibiting eglin mutants correspond substantially to those described above.

Inhalation preparations for treating the respiratory tract by intrapulmonary administration are, for example, aerosols or sprays that can distribute the pharmacological active ingredient in the form of drops of a solution or suspension. Preparations in which the pharmacological active ingredient is contained in solution contain, apart from this, a suitable propellant and also, if necessary, an additional solvent and/or a stabiliser. Instead of a propellant gas it is also possible to use compressed air, and this can be produced as required using a suitable compression and release device. Bird respirators, which are known and used in medicine, are especially suitable for administration; in this case a solution of the active ingredient is introduced into the device and vaporised with slight excess pressure and introduced into the lung as the patient breathes.

In the case of elastase-inhibiting eglin mutants, the dosage for a warm-blooded animal (human or animal) weighing approximately 70 kg, depending on age, individual condition and the nature of the disease, is from approximately 10 to approximately 30 mg per inhalation (once to twice daily) when administered via the intrapulmonary route, and from approximately 10 to approximately 1000 mg per day when administered intravenously, for example also by prolonged infusion. Therapeutically effective sputum and plasma concentrations, which may be determined by means of immunological processes, such as ELISA, range from 10 to 100 µg/ml (approximately 1 to 10 µmol/l).

The administration of trypsin-inhibiting eglin mutants is effected, for example, by parenteral, such as intravenous, intramuscular or subcutaneous, injection. A therapeutically effective amount is in a dosage range of approximately from 1 to 20 mg of active ingredient/kg of body weight. The pharmaceutical preparations contain the active ingredient in a concentration of from approximately 0.1 to approximately 100 mg/ml of solution. In addition to the active ingredient these pharmaceutical preparations also contain a buffer, for example a phosphate buffer (see above), and also sodium chloride, mannitol or sorbitol for setting the isotonicity.

PESTICIDES

The novel eglin mutants of formula I can also be used as proteinase inhibitors in the control of pests in plants. From the serine protease inhibitors occurring naturally in various genera of plants it is assumed that they represent an efficient protection against phytopathogenic insects, fungi and other microorganisms by inhibiting the serine proteases in the mentioned organisms. Furthermore, both monocotyledonous and dicotyledonous plants can be transformed with a DNA that codes for a heterologous protease inhibitor such as, for example, eglin B or C, or for an eglin mutant of formula I. The expression of the corresponding active proteinase inhibitors imparts to the transformed plants protection against attack by phytopathogens.

Methods that are known per se are available for the transformation of plants with suitable expression vectors that contain expression control sequences and a DNA coding for a compound of the invention, such as, for example, the cocultivation of protoplasts or isolated fragments of tissue with agrobacteria that contain the appropriate vectors, and the subsequent regeneration to complete plants, or the transfer of vectors with the aid of suitable unmodified or modified viruses, such as, for example, TMV (Tobacco Mosaic Virus) or CaMV (Cauliflower Mosaic Virus). Other methods are, for example, the direct transfer of isolated DNA (preferred in the case of monocotyledonous plants, such as maize, oats, barley, rice, sorghum, wheat, sugar cane and others) with the aid of PEG, by electroporation, by microinjection of DNA into isolated protoplasts, plant calli or embryos, or by microprojectile bombardment, and others.

DNA molecules that code for one of the compounds of the invention are suitable for transformation into plants. Preferred are those DNA molecules that code for an eglin mutant of formula I in which R is acetyl, W is Tyr, X is Thr, Y is Arg and Z is Asp. The protease-inhibiting action of the corresponding preferred eglin mutants can be examined in tests with the maize pathogen *Diabrotica virgifera* (Western corn root worm). The addition of the preferred eglin mutants to homogenates of intestinal tissue of the pathogen results in a marked inhibition of the proteolytic activity.

The invention relates especially to the eglin mutants described in the Examples, to the DNAs coding therefor, to expression plasmids containing such DNAs, to host microorganisms containing such expression plasmids and to the described processes for the production thereof.

The following Examples illustrate the invention without in any way implying any limitation.

EXPERIMENTAL PART

EXAMPLE 1

M13 Cloning of the Eglin C Gene

Approximately 0.5 μg of the 230 bp Eco RI-Bam HI fragment (containing the complete eglin C gene) is isolated from 10 μg of plasmid pML 147 by means of digestion with the restriction endonucleases Eco RI and Bam HI and subsequent electrophoresis in 1.5% low melting point agarose. This DNA fragment (10 ng) is mixed with 40 ng of M13mp8 DNA (pre-digested with Eco RI and Bam HI) and incubated in 50 mM tris-HCl pH 7.4, 10 mM MgCl2, 10 mM ATP, 10 mM dithiothreitol in the presence of 0.125 units of T4 DNA ligase in a volume of 15 μl [Zoller et al., Methods Enzym. 100, 468–500 (1983)]. The resulting solution is used to transform the $E.$ $coli$ strain JM101 (Zoller et al., see above). The transformation mixture is coated onto X-Gal (IPTG-indicator-agar) plates (Zoller et al., see above). 40 blue (wild type) and 650 colourless plaques are obtained.

EXAMPLE 2

Production of M13mp8 Single-Stranded DNA 2 ml of a culture of $E.$ $coli$ JM101 (grown in L medium: 10 g of bactotryptone, 5 g of bacto-yeast extract, 5 g of NaCl, 5 g of glucose, 0.1 g of ampicillin per liter, up to an $OD_{623}$=approx. 0.5) are inoculated with a colourless plaque (taken from the agar plate, see Example 1) and maintained for approximately 4 to 5 hours at 37° C. and 180 revs/min. Subsequently the grown culture is centrifuged for 5 minutes in an Eppendorf centrifuge. The supernatant is transferred into a fresh centrifuge tube, centrifuged again, 200 μl of 20% polyethylene glycol, 1.5M NaCl are added, and the whole is maintained at room temperature for 20 minutes and then centrifuged again. The supernatant is discarded and the pellet is dissolved in 100 μl of 50 mM tris-HCl pH 7.8, 1 mM EDTA (TE). The mixture is mixed with 50 μl of phenol/TE (15 minutes at room temperature) and then centrifuged for 5 minutes in an Eppendorf centrifuge. 10 μl of sodium acetate pH 6 and 3 volumes of absolute ethanol (250 μl) are added to 100 μl of supernatant and the whole is maintained at −20° C. overnight and then centrifuged as described above for 10 minutes. The pellet is washed with 1 ml of 80% ethanol and again centrifuged. The pellet is dried at room temperature for 10 minutes and then dissolved in 50 μl of TE. The solution contains approximately 5 μg of M13mp8 single-stranded DNA.

EXAMPLE 3

Production of the Gene Coding for [Arg45]-Eglin C a. Kinasing the Mutagenic Oligonucleotide The following nucleotide is produced by chemical synthesis for the mutagenesis:

$$5'\text{-dCTCCTTGTTACTCGGGACC-3'}$$

10 μl of the oligonucleotide (1 OD/ml=500 ng) are kinased in 20 μl of 0.07M tris-HCl pH 7.6, 0.01M MgCl2, 50 mM dithiothreitol with [−$^{32}$P]ATP and T4 polynucleotide kinase (Boehringer) [cf. Molecular Cloning, A Laboratory Manual, ed. T. Maniatis et al., page 125]. The kinased oligonucleotide is dissolved in 10 μl of TE (50 ng/μl).

b. Mutation of the Eglin C Gene $$3'\text{-GA GGA CAA TGA GAC CTG G-5'} + \quad (I)$$

$$5'\text{-CT CCT GTT ACT CGG GAC C-3'}$$
(oligo Primer)

$$\begin{array}{l}5'\text{-CT CCT GTT ACT CGG GAC C-3'} \\ 3'\text{-GA GGA CAA TGA GAC CTG G-5'} \\ \text{mutation}\end{array} \quad (II)$$

$$\begin{array}{l}^{42}\text{Pro Val Thr Arg Asp} \\ 5'\text{-CT CCT GTT ACT CGG GAC C-3'} \\ 3'\text{-GA GGA CAA TGA GCC CTG G-5'} \\ \text{MUTATION SCHEME}\end{array} \quad (III)$$

1 μg of the M13mp8 single-stranded DNA with 50 ng of the kinased oligonucleotide primer in 10 μl of 50 mM tris-HCl pH 7.8, 100 mM MgCl2 are maintained at 45° C. (30 minutes) and then at room temperature (5 minutes) ("annealing"). The following are then added to this mixture:

- 1 μl each of 10 mM dATP, dGTP, dCTP, dTTP,
- 1 μl of T4 DNA ligase
- 2 μl of 50 mM dithiothreitol
- 1 μl of 10 mM ATP
- 1 μl of 5 mg/ml gelatine
- 1 μl of 10×conc. Klenow buffer (0.66M tris-HCl pH 7.6, 50 mM MgCl2, 50 mM dithiothreitol)
- 1 μl of DNA polymerase (Klenow fragment)=2.5 units The mixture is maintained at 22° C. for 5 minutes and then at 15° C. for 16 hours and finally separated electrophoretically in 1% agarose. The resulting circular, double-stranded DNA is made visible with ethidium bromide and isolated from the gel by electroelution (approximately 10 ng in 15 μl TE).

5 μl (=approximately 3.5 ng) of the DNA obtained in this manner are transformed into the $E.$ $coli$ strain JM101 and coated onto X-Gal/IPTG indicator plates (see Example 1). Approximately 100 colourless plaques are obtained.

40 of these plaques are used to inoculate a 2 ml $E.$ $coli$ JM101 culture (see Example 2). After cultivation (Example 2), the $E.$ $coli$ cells are centrifuged off from the supernatant (contains phages and single-stranded DNA, the cell pellet already contains the corresponding mutated double-stranded DNA).

In each case 50 μl of the 40 phage supernatants are filtered over nitrocellulose, washed (2×TE), maintained under vacuum for 2 hours at 80° C. and examined according to Southern [J. Mol. Biol. 98, 503–517 (1975)] for the presence of the mutated DNA sequence (III, see scheme), using the oligonucleotide primer as radioactive probe (hybridisation). This results in 12 potential phage supernatants containing the [Arg45] eglin C gene. Four of these positive phage supernatants are diluted (approximately 1:105), mixed with *E. coli* strain JM101 and coated onto indicator agar. Phages of three each of the resulting plaques are isolated. The single-stranded DNA is isolated therefrom in the manner described above. These 12 single-stranded DNAs are sequenced in accordance with Sanger [Science 214, 1205 (1981); Proc. Natl. Acad. Sci. U.S.A. 74, 5463 (1977)]. All 12 single-stranded DNAs exhibit the desired mutated eglin C sequence.

In a minipreparation, the respective mutated double-stranded DNA ([Arg45] eglin C gene in plasmid M13mp8) is then prepared from the corresponding *E. coli* cell pellets (see above).

By restriction digestion with the restriction endonucleases Eco RI and Bam HI, the Eco RI-Bam HI insert containing the mutated gene is cut out from the vector, isolated and cloned in the vector pHRi 148/Eco RI/-Bam HI (European Patent Application No. 146785). The plasmid pJB618 resulting therefrom is isolated and transformed into the *E. coli* strain HB101. The strain transformed with plasmid pJB618 is designated *E. coli* HB101/pJB618.

EXAMPLE 4

Production of the Gene Coding for [Pro44]-Eglin C

The [Thr44]-[Pro44] mutation is carried out in a manner analogous to that described in Example 3. The mutagenic oligonucleotide used has the following structure

```
5'-CT CCT GTT CCT CTG GAC-3'
```

The mutation of the eglin C gene is represented in the following scheme.

3'-GA GGA CAA TGA GAC CTG-5' +   (I)

```
5'-CT CCT GTT CCT CTG GAC-3'
```
(oligo Primer)

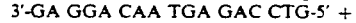
```
5'-CT CCT GTT CCT CTG GAC-3'       (II)
3'-GA GGA CAA TGA GAC CTG-5'
               mutation
```

```
                 42ProValProLeuAsp              (III)
5'-CT CCT GTT CCT CTG GAC-3'
3'-GA GGA CAA GGA GAC CTG-5'
```

On working up the mutation mixture 18 potential [Pro44]-eglin C mutants are obtained.

By cloning the [Pro44]-eglin C DNA in the vector pHRi 148/Eco RI/Bam HI, plasmid pJB591 is obtained in a manner analogous to that described in Example 3. The *E. coli* HB101 strain transformed with this plasmid is designated *E. coli* HB101/pJB591.

EXAMPLE 5

Production of the Gene Coding for [Arg45,Ser46]-Eglin C

The [Leu45,Asp46]-[Arg45,Ser46] mutation is carried out in a manner analogous to that described in Example 3. The mutagenic oligonucleotide used has the following structure:

```
5'-GTA ACG CAG AGA ACG AGT AAC AGG-3'
```

The mutation of the eglin C gene is represented in the following scheme.

3'-CAT TGC GTC CAG GTC TCA TTG TCC-5' +   (I)

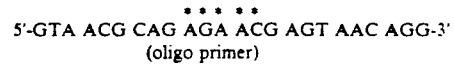
```
5'-GTA ACG CAG AGA ACG AGT AAC AGG-3'
```
(oligo primer)

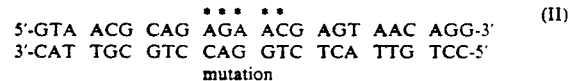
```
5'-GTA ACG CAG AGA ACG AGT AAC AGG-3'    (II)
3'-CAT TGC GTC CAG GTC TCA TTG TCC-5'
                mutation
```

```
5'-GTA ACG CAG AGA ACG AGT AAC AGG-3'    (III)
3'-CAT TGC GTC TCT TGC TCA TTG TCC-5'
      Leu47  Ser  Arg  Thr  Val43
```

On working up the mutation mixture 12 potential [Arg45,Ser46]-eglin C-mutants are obtained.

Plasmid pML147/b is obtained in a manner analogous to that described in Example 3 by cloning the [Arg45,Ser46]-eglin C-DNA into the vector pHRi148/Eco RI/Bam HI. The *E. coli* HB101 strain transformed with this plasmid is called *E. coli* HB101/pML147/b.

EXAMPLE 6

Culturing the Transformed *E. coli* Strains

The transformed *E. coli* HB101 strains are cultured overnight at 37° C. and 250 revs/min in 5 ml of L medium (see Example 2). 1 ml of this overnight culture is then transferred into 25 ml of M9 medium. M9 medium is composed of the following (per liter):

| | |
|---|---|
| $Na_2HPO_4.7H_2O$ | 13.25 g |
| $KH_2PO_4$ | 3.0 g |
| NaCl | 0.5 g |
| $NH_4Cl$ | 1.0 g |
| $CaCl_2.2H_2O$ | 0.015 g |
| $MgSO_4.7H_2O$ | 0.25 g |
| casamino acids | 2.5 g |
| vitamin $B_1$ | 0.0099 g |
| glucose | 5.0 g |
| ampicillin | 0.1 g |

Culturing is carried out at 37° C. and 250 revs/min. After 8 to 10 hours the culture has achieved the highest titre of eglin C mutants [determined by measuring the protease human leukocyte elastase according to U. Seemüller et al., Hoppe-Seyler's Z. Physiol. Chem. 358, 1105 (1977)].

EXAMPLE 7

Isolation and Purification of the Eglin Mutants

The overproducing *E. coli* cells are broken open mechanically using a Dynomill. The cell debris is centrifuged off in 30 minutes in a *Sorval centrifuge* at 9000 revs/min.

On account of the high stability of the eglin mutants towards acids, the majority of the foreign proteins in the supernatant can be eliminated by precipitation with approximately 20% acetic acid: 10 ml of 40% aqueous acetic acid is pipetted dropwise into 100 ml of supernatant within a period of 10 minutes. The acidic solution (pH 3.4) is stirred for 1 hour while cooling with ice. The precipitated foreign proteins and other cell components are centrifuged off in 30 minutes in a *Sorval centrifuge* at 9000 revs/min. The supernatant is lyophilised overnight in a Virtis Freezemobile.

The dried yellowish lyophilisate is dissolved in 10 ml of 10 mM tris-HCl pH 7.8 and briefly centrifuged to make the solution clear (Sorval SS34: 15000 revs/min, 10 minutes). The clear yellow supernatant is added to an equilibrated Sephadex G-50 superfine column (Pharmacia) 100 cm long and 2.5 cm in diameter. Elution is carried out with 10 mM tris-HCl pH 7.8 at a flow rate of max. 20 ml/h. Absorption of the eluate is recorded at 280 nm. 10 ml fractions are collected. The elution diagram shows a high peak (fractions 31–40), which contains the eglin mutants in question. The purity of the eglin mutants in these fractions is confirmed by SDS gel electrophoresis and HPLC. After gel filtration, the eglin mutants are approximately 99% pure.

The removal of the buffer from the eglin mutant fractions is carried out with an AMICON concentration cell having a YM-2 membrane (MWCO 2000). After ultrafiltration the samples are lyophilised again. A colourless powder is obtained (approximately 250 mg/100 ml Dynomill decomposition), which is stored at $-20°$ C.

EXAMPLE 8

Physicochemical Characterisation of the Eglin Mutants a. [Pro44]-Eglin C

The [Pro44]-eglin C purified according to Example 7 is subjected to a molecular weight determination by means of FAB-MS. The molecule ion peak (M-H$^+$) is ascertained at 8130.6. Accordingly the product obtained in accordance with the process is N-acetyl-[Pro44]-eglin C (theoretical value for M-H$^+$: 8130.07).

Tryptic degradation of the eglin mutant yields 7 fragments, of which only fragment 4, which contains the mutation Thr44-Pro44, differs from the corresponding fragments of N$^\alpha$-acetyl-eglin C (cf. European Patent Application No. 146785). The eglin mutant is thus to be designated N$^\alpha$-acetyl-[Pro44]-eglin C.

In the PAGE-SDS gel electrophoresis [cf. U.K. Laemmli, Nature 227, 680–685 (1970)] N$^\alpha$-acetyl-[Pro44]-eglin C behaves like N$^\alpha$-acetyl-eglin C.

b. [Arg45]-Eglin C

The molecular weight determination of the purified [Arg45]-eglin C gives a value of 8175.4 [M-H$^+$]. Thus, in this case too, an N-acetyl compound is present (theoretical value for M-H$^+$: 8175). The enzymatic degradation with trypsin makes it clear that the compound is N$^\alpha$-acetyl-[Arg45]-eglin C.

In the PAGE-SDS gel electrophoresis N$^\alpha$-acetyl-[Arg45]-eglin C also behaves in the same way as N$^\alpha$-acetyl-eglin C.

c. [Arg45,Ser46]-Eglin C

The molecular weight determination of the purified [Arg45,Ser46]-eglin C gives a value of 8148.7 [M-H$^+$]. Thus, in this case too, an N-acetyl compound is present (theoretical value for M-H$^+$: 8149.1). The tryptic degradation of the eglin mutant shows that the compound is N$^\alpha$-acetyl-[Arg45,Ser46]-eglin C.

In the PAGE-SDS gel electrophoresis N$^\alpha$-acetyl-[Arg45,Ser46]-eglin C also behaves in the same way as N$^\alpha$-acetyl-eglin C.

EXAMPLE 9

Kinetic Characterisation of the Eglin Mutants

The determination of the inhibition constants Ki is carried out according to N. Braun et al. [Biol. Chem. Hoppe-Seyler 368, 299–308 (1987)] by measuring the steady-state reaction rate of the release of p-nitroaniline from proteinase-inhibitor substrate mixtures. Only the inhibitor concentration is varied. Since the curve OD$_{405}$ vs. time was linear, the release of p-nitroaniline is entered at 10 to 20 minutes. Ki can be determined from the various slopes. The proteinases used are human leukocyte elastase (HLE), chymotrypsin and trypsin. Examples of inhibition constants are listed in the following table:

TABLE

| Inhibition constants | | |
|---|---|---|
| a. HLE: | | |
| | Eglin C | [Arg45]-eglin C |
| Ki (M) | 7.5 × 10$^{-11}$ | 1.1 × 10$^{-5}$ |
| b. chymotrypsin | | |
| Ki (M) | 4.4 × 10$^{-10}$ | 8 × 10$^{-9}$ |
| c. trypsin | | |
| Ki (M) | no inhibition | 1.3 × 10$^{-10}$ |

The results show that an eglin C mutant is obtained by exchanging Leu45 for Arg45, which mutant, in contrast to natural eglin C, is a very strong trypsin inhibitor but only a weak HLE inhibitor.

EXAMPLE 10

Expression of [Arg45]-Eglin C and N$^\alpha$-Acetyl-[Arg45]-Eglin C in Yeast

An expression system for foreign genes in yeast requires a strong yeast promoter, preferably an inducible promoter, and a yeast transcription termination signal in a tandem array separated by unique restriction sites for the insertion of foreign genes. An expression vector also contains yeast DNA sequences that allow autonomous replication in yeast and lead to a high plasmid copy number. These sequences preferably are yeast 2$\mu$ sequences. The vector also has a yeast selectable marker, preferably the yeast LEU2 gene, as well as pBR322 DNA sequences with the origin of replication and the ampicillin resistance gene for amplification in E. coli. Such a vector is a "shuttle" vector for use in E. coli and yeast.

A suitable expression system, as described above has been published in European Patent Application No. 100,561 and has been shown to be highly efficient in yeast. Foreign genes are expressed under the control of the inducible PHO5 promoter of yeast acid phosphatase. PHO5 promoter, foreign gene and PHO5 transcription termination signals are inserted in a tandem array in plasmid pJDB207. It contains yeast 2$\mu$ sequences, the yeast LEU2 gene, the E. coli origin of replication and the ampicillin resistance gene.

The expression plasmid pJDB207R/PHO5-[Arg45]EGL is constructed as follows:

a) Isolation of the pJDB207 Vector Fragment

Six $\mu$g of plasmid pJDB207R/IF ($\alpha$-3) (EP 100,561) are digested to completion with restriction endonuclease BamHI. The resulting DNA fragments of 6.85 kb and 1.15 kb in size are precipitated by ethanol and resuspended in 400 $\mu$l of 50 mM tris-HCl pH 8.0. 4.5 units of calf intestine alkaline phosphatase (Boehringer, Mannheim) are added. The mixture is incubated for 1 hour at 37° C. Subsequently, the phosphatase is inactivated by incubation at 65° C. for 1.5 hours. The solution is adjusted to 150 mM NaCl. The DNA solution is applied to a 100 $\mu$l bed of DE 52 (Whatman) anion exchanger equilibrated with 10 mM tris-HCl pH 7.5 containing 150 mM NaCl and 1 mM EDTA. After washing with the same buffer, the DNA is eluted with 400 μl of 10 mM tris-HCl pH 7.5, 1.5M NaCl, 1 mM EDTA and precipitated by ethanol. The large 6.85 kb BamHI fragment is separated from the small fragment on a 0.6% low melting agarose gel in tris-borate-EDTA buffer pH 8.3.

b) Isolation of a 534 bp PHO5 Promoter Fragment

Ten μg of plasmid p31/R (EP 100,561) are digested with restriction enconucleases EcoRI and BamHI. The resulting 3 fragments are separated on a 0.6% low melting agarose gel in tris-borate-EDTA buffer pH 8.3.

The 534 bp BamHI-EcoRI fragment is isolated which contains the PHO5 promoter including the mRNA start sites.

c) Isolation of a 230 bp DNA Fragment Containing the Coding Sequence for [Arg45]Eglin C Eight μg of plasmid pJB618 are digested with restriction endonucleases BamHI and EcoRI. The resulting 2 DNA fragments are separated on a 0.6% low melting agarose gel in tris-borate-EDTA buffer pH 8.3. The 230 bp fragment is isolated.

d) Ligation of DNA Fragments

Three DNA fragments described above (a-c) with appropriate sticky ends are ligated in one reaction. 0.1 pmole (0.45 μg) of the 6.85 kb BamHI vector fragment, 0,2 pmole (70 ng) of the 534 bp BamHI-EcoRI PHO5 promoter fragment and 0,2 pmole (29 ng) of the 230 bp EcoRI-BamHI fragment of pJB618 are ligated. All three DNA fragments are contained in small gel blocks of low melting agarose. The three pieces of agarose gel are pooled, liquified at 65° C. and diluted 2 times. The ligation is done in a total volume of 270 μl of 60 mM tris-HCl pH 7.5, 10 mM MgCl2, 10 mM DTT, 1 mM ATP with 16 units of T4 DNA ligase (Boehringer, Mannheim) at 15° C. for 16 hours. A 10 μl aliquot of the ligation mixture is added to 100 μl of calcium treated, transformation competent E. coli HB101 cells.

24 transformed, amp$^R$ colonies are grown individually in LB medium containing 100 μg/ml of ampicillin. Plasmid DNA is prepared according to the method of Holmes et al. [Anal. Biochem. 114, 193 (1981)] and is analysed by HindIII/EcoRI double digestion. The appearance of a 600 bp EcoRI-HindIII fragment indicates that the particular clone has the PHO5 promoter-[Arg45]eglin C-DNA fragment inserted in the expression vector in the correct orientation. As expected, about 50% of the clones have an insert in the right orientation. One of these clones is isolated and referred to as pJDB207R/PHO5-[Arg45]EGL.

e) Transformation of *Saccharomyces cerevisiae* GRF18

Plasmid pJDB207R/PHO5[Arg45]EGL is introduced into *Saccharomyces cerevisiae* strain GRF18 (α, his3-11, his3-15, Leu2-3, Leu2-112, can$^R$) using the transformation protocol described by Hinnen et al. [Proc. Natl. Acad. Sci. U.S.A. 75, 1929 (1978)]. Transformed yeast cells are selected on yeast minimal media plates deficient in leucine. Single transformed yeast colonies are isolated and referred to as *Saccharomyces cerevisiae* GRF18/pJDB207R/PHO5-[Arg45]EGL.

f) Fermentation of *Saccharomyces cerevisiae* GRF18/pJDB207R/PHO5-[Arg45]EGL and Recovery of [Arg45]-Eglin C and N$^α$-Acetyl-[Arg45]-Eglin C Cells of *Saccharomyces cerevisiae* GRF18/pJDB207R/PHO5-[Arg45]-EGL are grown in 3 l minimal medium with 0,03 g/l KH$_2$PO$_4$ at 30° C. in a Mini-Bioreactor and harvested at an OD$_{600}$ of 1.9.

[Arg45]-eglin C and N$^α$-acetyl-[Arg45]-eglin C are expressed in a ratio of about 2:1 (w/w). Both products can be isolated from yeast cell homogenates according to the method given for *E. coli* in example 7.

EXAMPLE 11

Pharmaceutical Preparation

A solution containing N$^α$-acetyl-[Arg45]-eglin C and produced in accordance with Example 7 is dialysed against a 0.9% NaCl solution. The concentration of the solution is then adjusted to 1 mg/ml or 10 mg/ml by dilution with the same NaCl solution. These solutions are sterilised by ultrafiltration (membrane with 0.22 μm pores).

The sterilised solutions can be used directly for intravenous administration and for prolonged drip infusion.

Deposit of Microorganisms

The strain *E. coli* HB101/pML147 was deposited on 28th Jan. 1988 at the Deutsche Sammlung von Mikroorganismen (DSM), Mascheroder Weg 1b, D-3300 Braunscheweig, under the number DSM 4380.

What is claimed is:

1. The protease inhibitor N$^α$-Acetyl/Arg45/-eglin C or a pharmaceutically acceptable salt thereof.

2. A pharmaceutical composition comprising the protease inhibitor of claim 1.

3. A method of inhibiting trypsin in a mammal in need thereof, comprising administering to the mammal a therapeutically effective amount of the protease inhibitor of claim 1.

* * * * *